(12) United States Patent
Lill

(10) Patent No.: US 8,028,834 B2
(45) Date of Patent: Oct. 4, 2011

(54) MEDICAL TUBING BAG

(75) Inventor: Robert J. Lill, Wichita, KS (US)

(73) Assignees: Robert J. Lill, Wichita, KS (US); Susan Seefeld Lill, Wichita, KS (US)

(*) Notice: Subject to any disclaimer, the term of this patent is extended or adjusted under 35 U.S.C. 154(b) by 1378 days.

(21) Appl. No.: 11/586,941

(22) Filed: Oct. 26, 2006

(65) Prior Publication Data

US 2008/0169372 A1    Jul. 17, 2008

(51) Int. Cl.
    *A61B 19/02*    (2006.01)
(52) U.S. Cl. ........................................ 206/438; 206/702
(58) Field of Classification Search ........... 206/438.388, 206/303, 410, 702, 438; 383/72–76, 119, 383/22, 23, 26, 41, 61.4, 63; 128/877; 150/154
    See application file for complete search history.

(56) References Cited

U.S. PATENT DOCUMENTS

| 3,491,373 | A | * | 1/1970 | Finis, Jr. ............................ 2/66 |
| 4,383,528 | A | | 5/1983 | Eppolito |
| 4,438,764 | A | | 3/1984 | Eppolito |
| 4,688,674 | A | * | 8/1987 | Stirtz ............................ 206/388 |
| 4,739,913 | A | | 4/1988 | Moore |
| 5,139,187 | A | * | 8/1992 | Fowler ........................ 224/576 |
| 5,341,933 | A | | 8/1994 | Willows |
| 5,370,113 | A | | 12/1994 | Parsons |
| 5,392,786 | A | * | 2/1995 | Lewis et al. ................... 128/877 |
| 5,676,135 | A | | 10/1997 | McClean |
| 5,839,631 | A | | 11/1998 | Hebert et al. |
| 6,003,744 | A | | 12/1999 | Culjak |
| 6,085,695 | A | * | 7/2000 | Miller et al. .................. 119/795 |
| 6,126,054 | A | * | 10/2000 | Riemer ........................ 224/601 |
| 6,142,192 | A | | 11/2000 | Dickinson |
| 6,478,157 | B1 | * | 11/2002 | Witt et al. ..................... 206/702 |
| 6,880,702 | B1 | | 4/2005 | Colorado |
| 7,104,491 | B2 | | 9/2006 | Vinding |
| 2002/0104860 | A1 | | 8/2002 | Warner |
| 2005/0205456 | A1 | * | 9/2005 | Meyer et al. .................. 206/525 |

* cited by examiner

*Primary Examiner* — Mickey Yu
*Assistant Examiner* — Jenine Pagan
(74) *Attorney, Agent, or Firm* — Lathrop & Gage LLP

(57) ABSTRACT

A medical tubing bag disclosed herein includes a housing having an open interior area and generally opposed first and second ends defining respective first and second openings. A first guide is adjacent the first opening for guiding tubing in and out of the first opening. In an embodiment, the first opening has a center axis being offset from a center axis of the first guide. In an embodiment, a second guide is inwardly adjacent the second opening for guiding tubing in and out of the open interior area. In an embodiment, a medical system includes a medical tubing bag, a medical device, and medical tubing. The tubing has a first end coupled to the medical device, the tubing extends into the medical bag, and the tubing continues from the medical bag to a user.

1 Claim, 3 Drawing Sheets

MEDICAL TUBING BAG

BACKGROUND

Medical tubing, including oxygen tubing and other types of tubing, is commonly used to connect a user to a medical device (e.g., an oxygen source). When a user is moving or being moved in relation to the medical device, there is a strong tendency for the tubing to become kinked, unconnected from the medical device, and/or heaped or strewn in inconvenient and potentially dangerous manners.

Various devices have been created to increase the mobility of people using medical tubing. Of these, many provide ways for coupling the medical tubing and the medical device to the user, such as those disclosed in U.S. Pat. Nos. 4,383,528; 4,438,764; 4,739,913; 5,370,113; 5,676,135; and 6,003,744 and in U.S. Pat. Publication No. 2002/0104860. While these may be useful in situations where the user is moving over large areas, they are not ideal for users moving over smaller areas because the user is having to carry or otherwise maneuver the weight of the medical device unnecessarily. Previously, there has not been a convenient way for the user to travel within a defined radius of a generally-stationary medical device without either: 1) enduring problems (such as those mentioned above) with the medical tubing that connects the user to the medical device; or 2) exerting excessive attention and energy to maintain the medical tubing in an orderly fashion.

SUMMARY

A medical tubing bag that organizes medical tubing and allows a user to easily move within a defined radius of a generally-stationary medical device would increase mobility and user safety by eliminating problems such as those described above. Accordingly, medical tubing bags are disclosed herein. A medical tubing bag of one embodiment includes a housing having an open interior area and generally opposed first and second ends defining respective first and second openings. A first guide is adjacent the first opening for guiding medical tubing in and out of the first opening.

In an embodiment, a medical tubing bag includes a housing having an open interior area and generally opposed first and second ends defining respective first and second openings. A first guide is adjacent the first opening for guiding medical tubing between the open interior area and an area outside the housing. The first opening has a center axis, and the first guide has a center axis; the center axis of the first opening is offset from the center axis of the first guide.

In an embodiment, a medical tubing bag for storing medical tubing that connects a user to a medical device is provided. The medical tubing bag includes a housing having an open interior area and generally opposed first and second ends defining respective first and second openings. A first guide is inwardly adjacent the first opening for guiding medical tubing into and out of the open interior area, and a second guide is inwardly adjacent the second opening for guiding medical tubing into and out of the open interior area.

In an embodiment, a medical system incorporating a medical tubing bag is provided. The medical system includes the medical tubing bag, a medical device, and medical tubing. The medical tubing bag includes a housing having an open interior area and generally opposed first and second ends defining respective first and second openings. A first guide is adjacent the first opening, and a second guide is adjacent the second opening. The medical tubing has a first end coupled to the medical device, and the medical tubing extends from the medical device through the first opening and the first guide and into the open interior area. The medical tubing continues from the open interior area through the second guide and the second opening and to a user.

DETAILED DESCRIPTION

Figure 1:
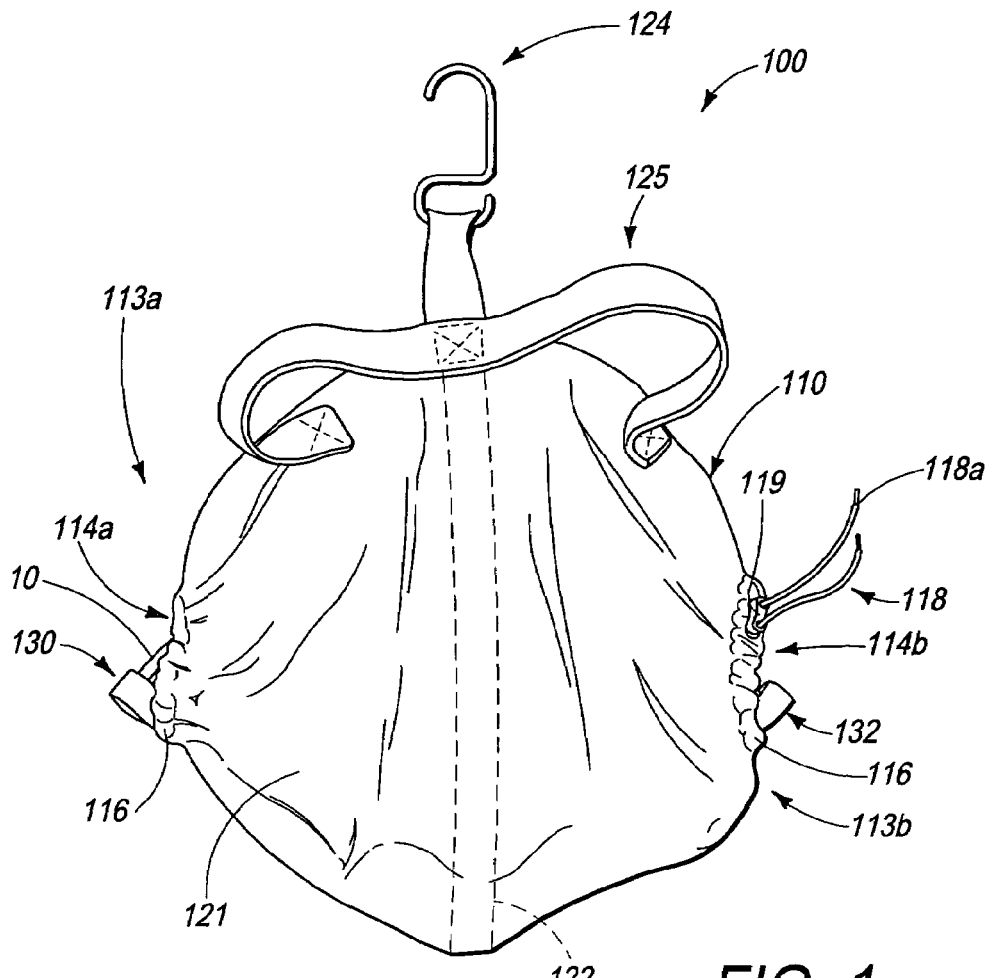
FIG. 1 shows a side view of a medical tubing bag according to an embodiment.
Figure 2:
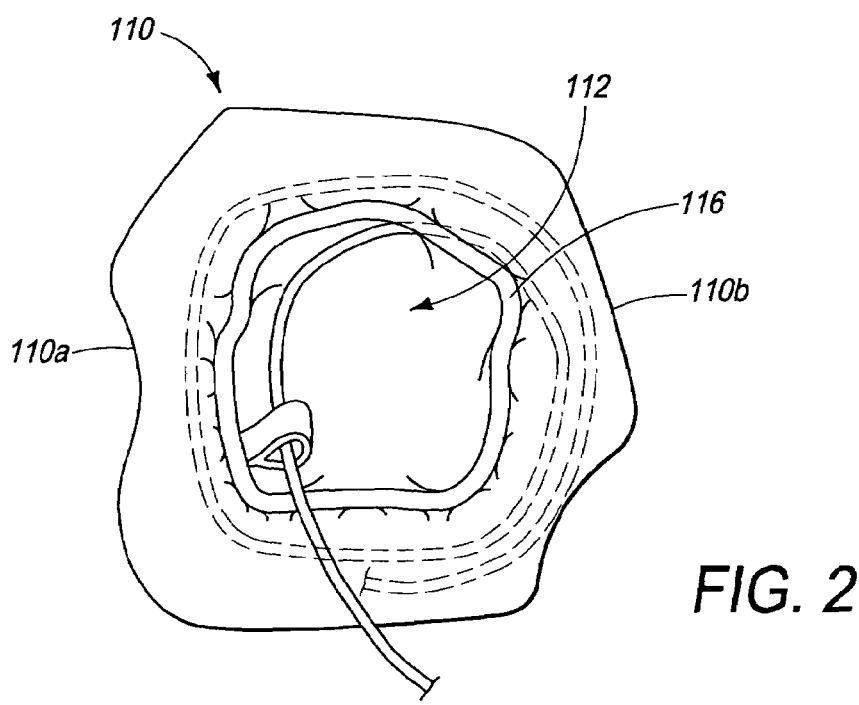
FIG. 2 shows an end view of the medical tubing bag of FIG. 1.
Figure 3:
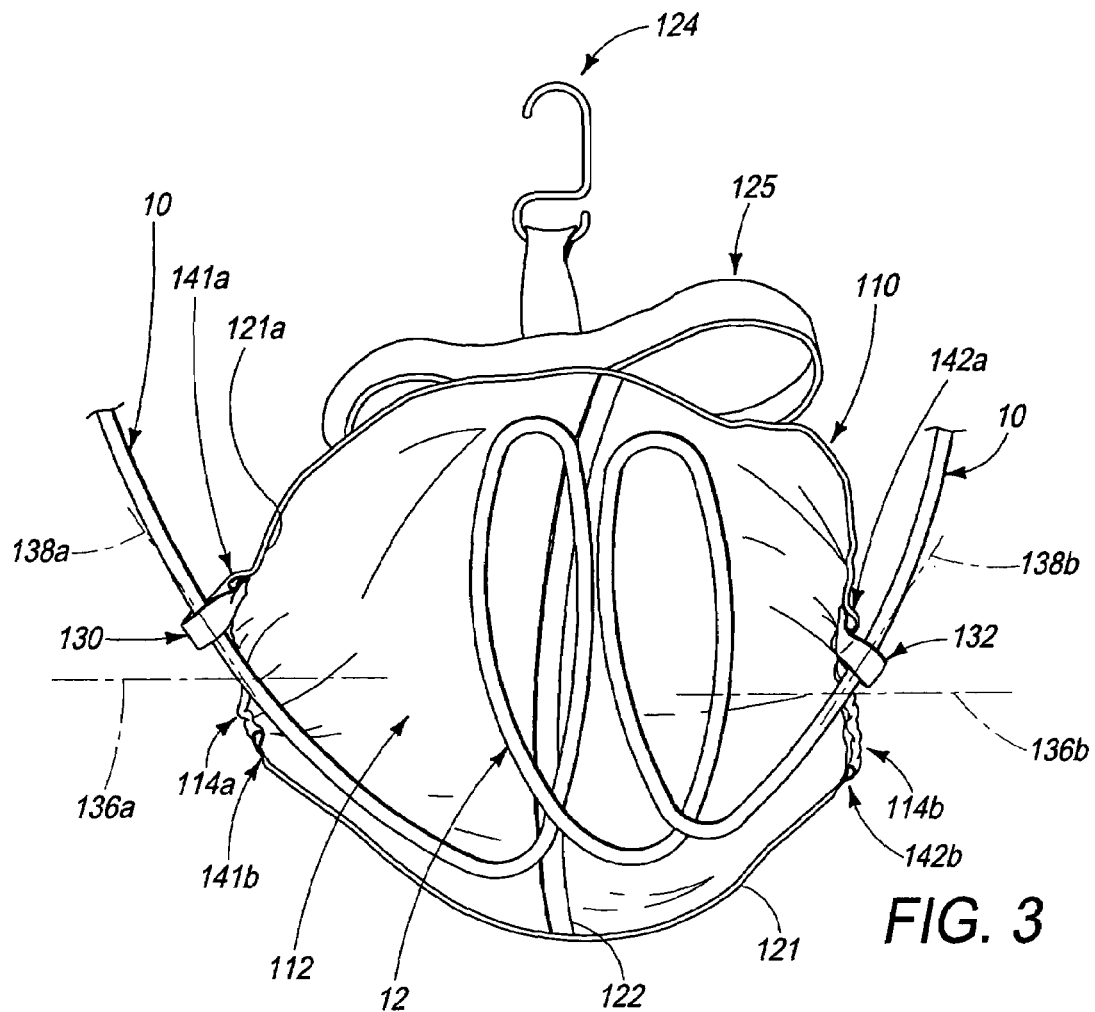
FIG. 3 shows a sectional view of the medical tubing bag of FIG. 1.

FIG. 1 through 3 show a medical tubing bag 100. The medical tubing bag 100 has a housing 110 that defines an open interior area 112. The housing 110 has generally opposed first and second ends 113a, 113b defining respective first and second openings 114a, 114b. The first and second openings 114a, 114b have respective perimeters that may be elastic or non-elastic. To make a respective perimeter elastic, for example, an elastic member 116 may be coupled to the housing adjacent a respective opening 114a, 114b.

The first and/or second opening 114a, 114b may be adjustable. For example, FIG. 1 shows a cord 118 that is slidably secured to the housing 110 adjacent a majority of the perimeter of the second opening 114b; a locking mechanism 119 is coupled to the cord 118 so that one or more end 118a of the cord 118 may be pulled to draw the cord 118 through the locking mechanism 119 and reduce the size of the second opening 114b. To enlarge the size of the second opening 114b, the cord 118 may be pulled through the locking mechanism 119 so that the cord ends 118a approach the locking mechanism 119. It should be appreciated that the cord 118 may be used without the locking mechanism 119 and that other adjustment devices may be used, such as a tightening strap, complementary fasteners spaced about the respective opening perimeter, etc.

The housing 110 may include a flexible fabric 121, as shown throughout the drawings, though a rigid material (e.g., plastic, wood, metal, etc.) may alternately be used. A rib 122 may be coupled to the flexible fabric 121 to maintain at least a portion of the fabric 121 at an uncollapsed configuration. In other words, the rib 122 may keep opposed sides 110a, 110b of the housing 110 separated from one another. The rib 122 may be generally centered between the first and second ends 113a, 113b of the housing 110 (FIG. 1), or the rib 122 may be offset closer to one of the ends 113a, 113b. As shown in FIG. 1, a perimeter of the fabric 121 at the rib 122 may be larger than the respective perimeters of the first and second openings 114a, 114b. The housing 110 may include an external hook 124 and/or an external handle 125 to facilitate carrying or hanging the tubing bag 100, for example.

A first guide 130 is coupled to the housing 110; the first guide 130 is adjacent the first opening 114a for guiding medical tubing 10 in and out of the first opening 114a (i.e., between the open interior area 112 and an area outside the housing 110). A second guide 132 may be coupled to the housing 110 adjacent the second opening 114b. In one embodiment, the second guide 132 may be used for guiding medical tubing 10 in and out of the second opening 114b (i.e., between the open interior area 112 and an area outside the housing 110). In another embodiment, the second guide 132 may act as a brake to generally keep an amount of medical tubing 10 from moving relative to the housing 110. For example, the second guide 132 may be sized so that a coupler connecting the medical tubing 10 with medical tubing 10 associated with a canula may not pass therethrough. If both the first and second guides 130, 132 are used to guide medical tubing 10 between the open interior area 112 and an area outside the housing 110, it may be desirable to add a braking device (e.g., a strap or loop) inside the open interior area 112 to keep an amount of medical tubing from moving relative to the housing 110.

The guides 130, 132 may be inwardly adjacent the respective openings 114a, 114b (i.e., attached to an inner surface 121a of the fabric 121 or to the elastic member 116 so as to be at least partially concealed by the housing 110, for example) or otherwise adjacent the respective openings 114a, 110b. Among other things, an inwardly adjacent configuration may be useful in guiding medical tubing 10 into the interior area 112 and in keeping the guides 130, 132 from becoming snared on various items.

As shown in FIG. 3, the first opening 114a has a center axis 136a, the second opening 114b has a center axis 136b, the first guide 130 has a center axis 138a, and the second guide 132 has a center axis 138b. By offsetting the center axis 138a of the first guide 130 from the center axis 136a of the first opening 114a so that the axes are not parallel, the medical tubing 10 may be more easily guided in and out of the first opening 114a and the medical tubing 10 may be prompted to form a coil 12 inside the housing 110. Similarly, offsetting the center axis 138b of the second guide 132 from the center axis 136b of the second opening 114b may allow the medical tubing 10 to be more easily guided in and out of the second opening 114b, forming a coil 12 inside the housing 110. Though not specifically shown in the drawings, the first and second guides 130, 132 may be coupled to the housing 110 so that their center axes 138a, 138b are generally perpendicular with the respective center axes 136a, 136b of the openings 114a, 114b when the medical tubing 10 is separated from the guides 130, 132.

Figure 4:
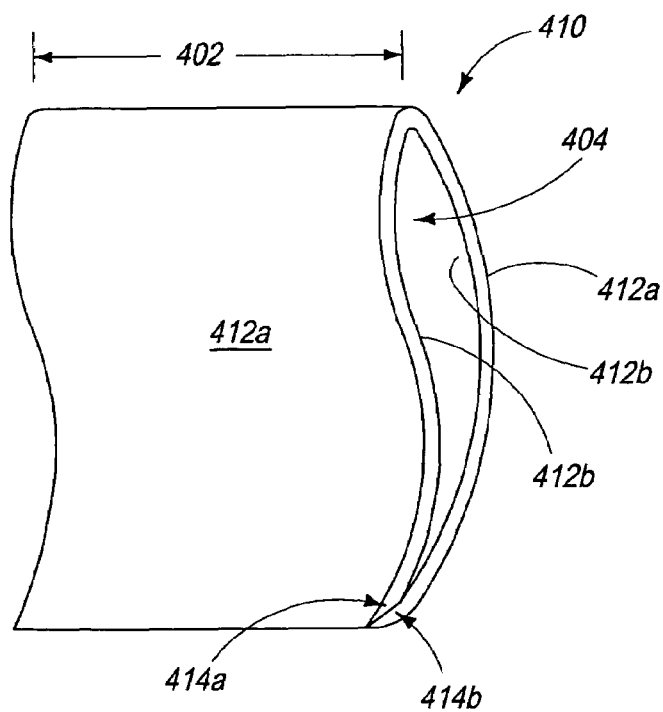
FIG. 4 shows a guide according to an embodiment for use in the medical tubing bag of FIG. 1.

To take advantage of offsetting the first and second guides 130, 132 as described above, it may be desirable to use first and second guides 130, 132 having a significant amount of depth. For example, a guide 400 that is representative of the first guide 130 and the second guide 132 according to an embodiment is shown in FIG. 4. The guide 400 has a depth 402 and an interior diameter 404 sized to pass the medical tubing 10 therethrough. By having the depth 402 at least as large as the interior diameter 404, the offsetting may be fully taken advantage of, though other depth/diameter configurations may also be appropriate.

While various guides 130, 132 may be used, the guide 400 includes a strap 410 having inner and outer surfaces 412a, 412b and first and second ends 414a, 414b. The inner surface 412a at the first end 414a is coupled to the inner surface 412a at the second end 414b (e.g., through stitching, adhesive, etc.) to form a flexible teardrop configuration. The first and second ends 414a, 414b of the strap 410 are operatively coupled to the housing 110 (e.g., through stitching, adhesive, etc.), and as discussed above, the strap 410 may extend into the open interior area 112. In one embodiment, the strap 410 is constructed of a cloth material, though nylon and/or other appropriate materials may be used.

Returning to FIG. 3, the first opening 114a has an uppermost point 141a and a lowermost point 141b; the second opening 114b has an uppermost point 142a and a lowermost point 142b. The first guide 130 may be positioned closer to the uppermost point 141a of the first opening 114a than to the lowermost point 141b to allow the medical tubing 10 to be more easily guided in and out of the first opening 114a from a position above the housing 110. The second guide 132 may be positioned closer to the uppermost point 142a of the second opening 114b than to the lowermost point 142b to allow the medical tubing 10 to be more easily guided in and out of the second opening 114b from a position above the housing 110. This described positioning of the first and second guides 130, 132 may be desirable, for example, if the user has to reach down (e.g., to a location below the shoulder) to adjust the relationship between the medical tubing bag 100 and the medical tubing 10, which may often be necessary. If the second guide 132 is being used as a brake as mentioned above, the positioning of the second guide 132 may not be as critical as when the second guide 132 is not being used as a brake.

Figure 5:
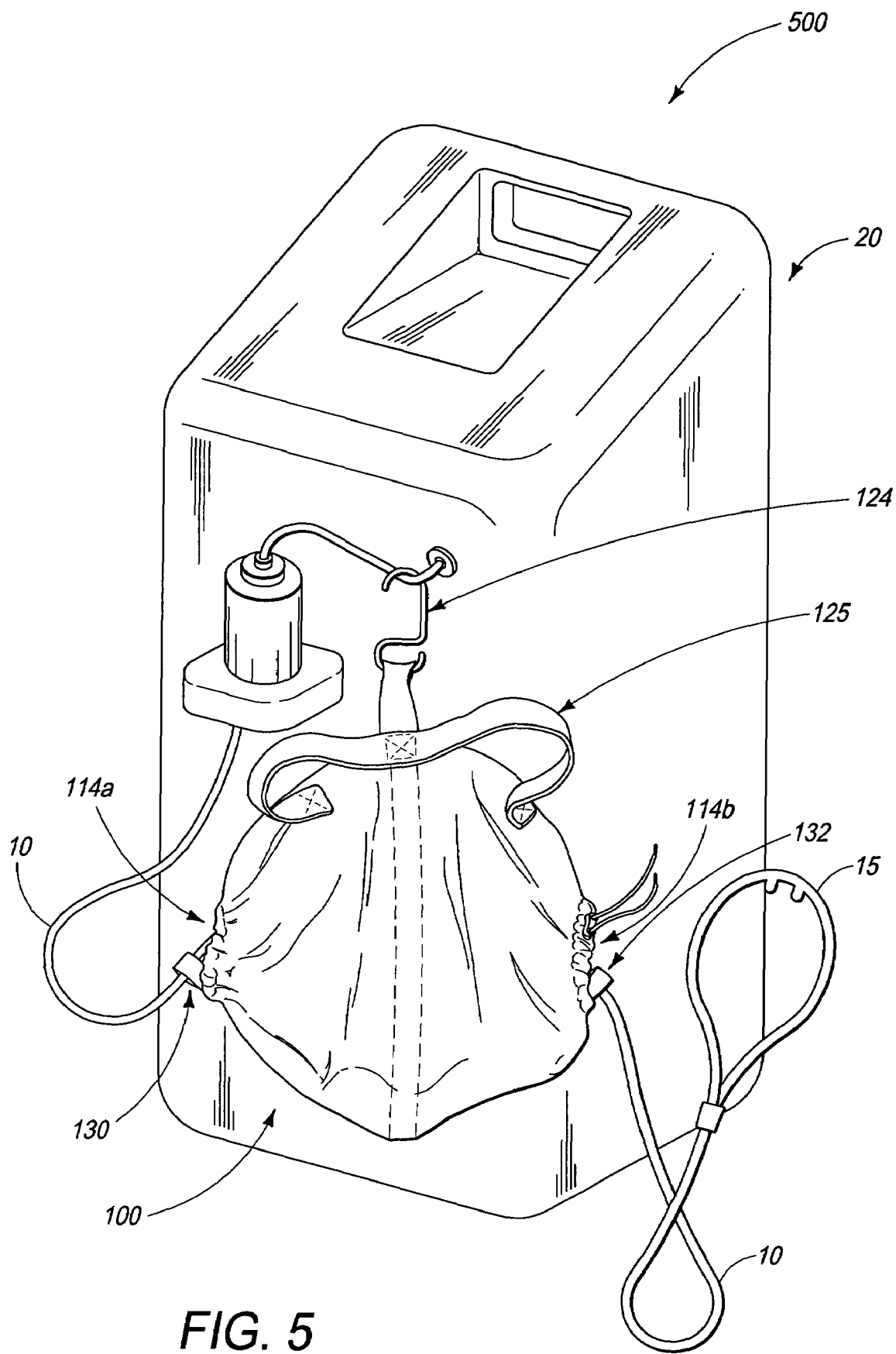
FIG. 5 shows a medical system incorporating the medical tubing bag of FIG. 1.

FIG. 5 shows a medical system 500 incorporating the medical tubing bag 100 described above, the medical tubing 10, and a medical device 20 (e.g., an oxygen concentrator, etc.). More particularly, a first end 10a of the medical tubing 10 is coupled to the medical device 20. The medical tubing 10 extends from the medical device 20 through the first opening 114a in the medical tubing bag 100, through the first guide 130, and into the open interior area 112. The medical tubing 10 further extends from the open interior area 112, through the second guide 132 and the second opening 114b, and to a user (e.g., through a canula 15). The amount of the medical tubing 10 in the open interior area 112 is modifiable by moving the tubing 10 through the first guide 130 and the first opening 114a and optionally by moving the tubing 10 through the second guide 132 and the second opening 114b as described above. A user may want to remove tubing 10 from the interior area 112 when moving further from the medical device 20 and introduce tubing 10 to the interior area 112 when moving closer toward the medical device 20, for example.

By forming a coil 12 inside the interior area 112 with excess medical tubing 10 as discussed above, the medical tubing 10 may be averse to kinking, easily adjusted, and generally out of the way. The first and/or second opening 114a, 114b of the medical tubing bag 100 may be adjusted as described above to allow quick access to the interior area 112 and tubing 10 housed therein. If the second guide 132 is operating as a brake as described above, it may be desirable for the first opening 114a to be adjustable, though this need not be the case. The external hook 124 may be used to attach the medical tubing bag 100 to a separate object as shown in FIG. 5 (e.g., a walker, a bed, a chair, etc.), and the external handle 125 may be used to carry the tubing bag 100.

Those skilled in the art appreciate that variations from the specified embodiments disclosed above are contemplated herein. The description should not be restricted to the above embodiments, but should be measured by the following claims.

The invention claimed is:

1. A bag for a medical oxygen tubing comprising:
a flexible fabric body defining a chamber for receiving a plurality of loops of the medical oxygen tubing;
a receiving end of the body having a medical-tube-receiving mouth which is completely lined by an elastic material to elastically compel the medical-tube-receiving mouth in a partially-closed state;
a distribution end of the body having a medical-tubing-distribution mouth, the distribution mouth being optionally openable and constrictable using a cinch arrangement, the cinch arrangement including a cord which is received into a sleeve, the sleeve extending almost all the way around the medical-tubing-distribution mouth, a pair cord ends being received through a locking mechanism which, the locking mechanism being configured such that upon a user's tugging of the cord ends, a size of medical-tubing-distribution mouth will be reduced, and upon a user's pulling outward on opposite sides of the medical-tubing-distribution mouth, the size of the medical-tubing-distribution mouth will be increased;

a first guide located on the medical-tube-receiving mouth, the first guide being formed from a looped strap, wherein the ends of the strap are doubled over and secured to the bag, the looped strap presenting a tear-drop-shaped through hole, the tear-drop-shaped through hole being sized to be slightly larger than the medical oxygen tubing such that the medical oxygen tubing can resistively slide in and out of the bag though the tear-drop-shaped through hole and form the plurality of loops;

a peripheral rib at a midsection of the flexible fabric body, the rib being constructed to maintain the flexible fabric body in an uncollapsed state, said peripheral rib defining a plane; a cloth strap handle attached to the bag in two locations, one on either side of the peripheral rib; and a metal hook attached at the midsection of the bag and extending in said plane of the peripheral rib.

\* \* \* \* \*